(12) United States Patent
Schuman et al.

(10) Patent No.: US 11,058,368 B2
(45) Date of Patent: *Jul. 13, 2021

(54) DISTRIBUTED HEALTHCARE COMMUNICATION SYSTEM

(71) Applicant: Hill-Rom Services, Inc., Batesville, IN (US)

(72) Inventors: Richard J. Schuman, Cary, NC (US); Patricia A. Glidewell, Cary, NC (US); Erik E. Roehl, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,009

(22) Filed: Apr. 6, 2020

(65) Prior Publication Data

US 2020/0229776 A1    Jul. 23, 2020

Related U.S. Application Data

(63) Continuation of application No. 16/398,775, filed on Apr. 30, 2019, now Pat. No. 10,638,983, which is a
(Continued)

(51) Int. Cl.
  *G08B 5/22* (2006.01)
  *A61B 5/00* (2006.01)
  (Continued)

(52) U.S. Cl.
  CPC ............ *A61B 5/7465* (2013.01); *A61B 5/002* (2013.01); *A61B 5/0022* (2013.01); *A61B 5/746* (2013.01);
  (Continued)

(58) Field of Classification Search
  CPC ..... G06F 19/327; G06F 3/048; A61B 5/7465; G08B 5/22
  See application file for complete search history.

(56) References Cited

U.S. PATENT DOCUMENTS 2,330,356 A    9/1943 Belliveau
2,335,524 A    11/1943 Lomax
(Continued)

FOREIGN PATENT DOCUMENTS

EP    1463269    9/2004
EP    1 623 666 A2    2/2006
(Continued)

OTHER PUBLICATIONS

Hill-Rom A Hillenbrand Industry, The COMposer® System Installation Manual, 2003.
(Continued)

*Primary Examiner* — Toan N Pham
(74) *Attorney, Agent, or Firm* — Barnes & Thornburg LLP

(57) ABSTRACT

A graphical audio station of a nurse call system is operable to permit a user to perform one or more of the following functions: establish a two-way voice communication link with another computer device in another patient and/or with a another computer device located in another staff work area and/or with a wireless communication device carried by caregiver and/or with a telephone of the healthcare facility; broadcast a voice page to a group of other selected computer devices; compose and send a text message to a portable device that is carried by a caregiver and that has wireless communication capability; browse web pages and/or view multimedia content, such as videos, hosted on servers of the healthcare facility and/or that are accessible via the Internet; view and/or acknowledge and/or answer and/or cancel alerts or nurse calls originating in a plurality of patient rooms.

20 Claims, 7 Drawing Sheets

Related U.S. Application Data continuation of application No. 15/939,762, filed on Mar. 29, 2018, now Pat. No. 10,307,113, which is a continuation of application No. 15/332,699, filed on Oct. 24, 2016, now Pat. No. 9,955,926, which is a continuation of application No. 15/053,303, filed on Feb. 25, 2016, now Pat. No. 9,517,035, which is a continuation of application No. 14/091,392, filed on Nov. 27, 2013, now Pat. No. 9,299,242, which is a continuation of application No. 12/369,813, filed on Feb. 12, 2009, now Pat. No. 8,598,995.

(60) Provisional application No. 61/066,877, filed on Feb. 22, 2008, provisional application No. 61/066,882, filed on Feb. 22, 2008, provisional application No. 61/066,883, filed on Feb. 22, 2008, provisional application No. 61/066,918, filed on Feb. 22, 2008, provisional application No. 61/145,306, filed on Jan. 16, 2009.

(51) Int. Cl.
*H04L 29/08* (2006.01)
*G16H 40/20* (2018.01)
*G08B 25/00* (2006.01)
*G08B 25/01* (2006.01)
*G08B 7/06* (2006.01)
*G06F 3/048* (2013.01)

(52) U.S. Cl.
CPC ............ *G06F 3/048* (2013.01); *G08B 5/222* (2013.01); *G08B 7/06* (2013.01); *G08B 25/00* (2013.01); *G08B 25/016* (2013.01); *G16H 40/20* (2018.01); *H04L 67/12* (2013.01); *H04L 67/18* (2013.01)

(56) References Cited

U.S. PATENT DOCUMENTS

| | | |
|---|---|---|
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Chahariiran |
| 4,907,845 A | 3/1990 | Wood |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,075,523 A | 12/1991 | Ford |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,140,309 A | 8/1992 | Gusakov |
| 5,153,584 A | 10/1992 | Engira |
| 5,235,258 A | 8/1993 | Schuerch |
| 5,266,944 A | 11/1993 | Carroll et al. |
| 5,276,680 A | 1/1994 | Messenger |
| 5,291,399 A | 3/1994 | Chaco |
| 5,319,355 A | 6/1994 | Russek |
| 5,319,363 A | 6/1994 | Welch et al. |
| 5,327,592 A | 7/1994 | Stump |
| 5,351,439 A | 10/1994 | Takeda et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,430,900 A | 7/1995 | Kim |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,511,256 A | 4/1996 | Capaldi |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,564,108 A | 10/1996 | Hunsaker et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,600,214 A | 2/1997 | Fromson |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,649,833 A | 7/1997 | Pfeuffer et al. |
| 5,650,769 A | 7/1997 | Campana, Jr. |
| 5,650,770 A | 7/1997 | Schlager et al. |
| 5,664,270 A | 9/1997 | Bell et al. |

(56) References Cited

U.S. PATENT DOCUMENTS

| | | |
|---|---|---|
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,714,548 A | 2/1998 | Ma et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,781,921 A | 7/1998 | Nichols |
| 5,787,528 A | 8/1998 | Antinori |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,901,391 A | 5/1999 | Kato |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,956,539 A | 9/1999 | Fitterman et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |
| 6,037,723 A | 3/2000 | Shafer et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Tumbull et al. |
| 6,093,146 A | 7/2000 | Filangeri |
| 6,097,308 A | 8/2000 | Albert et al. |
| 6,101,644 A | 8/2000 | Gagneur et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,483,264 B1 | 11/2002 | Shafer et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,105 B2 | 4/2003 | Chea, Jr. et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,224 B1 | 5/2003 | Kung et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,358 B1 | 12/2003 | Oldagiri |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,693,514 B2 | 2/2004 | Perea, Jr. et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,607 B2 | 7/2004 | Engler |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |

(56) References Cited

U.S. PATENT DOCUMENTS

| | | |
|---|---|---|
| 6,788,206 B1 | 9/2004 | Edwards |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,864,795 B2 | 3/2005 | Smith et al. |
| 6,868,256 B2 | 3/2005 | Dooley et al. |
| 6,870,484 B1 | 3/2005 | Brinsfield et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,892,083 B2 | 5/2005 | Shostak |
| 6,904,161 B1 | 6/2005 | Becker et al. |
| 6,909,974 B2 | 6/2005 | Yung et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 6,968,375 B1 | 11/2005 | Brown |
| 6,982,639 B2 | 1/2006 | Brackett et al. |
| 6,988,989 B2 | 1/2006 | Weiner et al. |
| 6,998,986 B2 | 2/2006 | Smith |
| 7,020,921 B2 | 4/2006 | Wang |
| 7,023,821 B2 | 4/2006 | Wotherspoon et al. |
| 7,038,584 B2 | 5/2006 | Carter |
| 7,053,767 B2 | 5/2006 | Petite et al. |
| 7,061,396 B1 | 6/2006 | Conrad et al. |
| 7,068,143 B2 | 6/2006 | Doering et al. |
| 7,071,820 B2 | 7/2006 | Callaway |
| 7,079,036 B2 | 7/2006 | Cooper et al. |
| 7,088,235 B1 | 8/2006 | Carricut |
| 7,092,376 B2 | 8/2006 | Schuman |
| 7,107,642 B2 | 9/2006 | Wong et al. |
| 7,138,902 B2 | 11/2006 | Menard |
| 7,151,457 B2 | 12/2006 | Riley et al. |
| 7,160,133 B2 | 1/2007 | Karadimas et al. |
| 7,248,881 B2 | 7/2007 | Shostak |
| 7,263,669 B2 | 8/2007 | Denholm |
| 7,275,220 B2 | 9/2007 | Brummel et al. |
| 7,290,299 B2 | 11/2007 | Votel |
| 7,292,135 B2 | 11/2007 | Bixler et al. |
| 7,299,512 B2 | 11/2007 | Cavalier et al. |
| 7,301,451 B2 | 11/2007 | Hastings |
| 7,307,522 B2 | 12/2007 | Dawson |
| 7,310,541 B2 | 12/2007 | Shostak |
| 7,319,386 B2 | 1/2008 | Collins, Jr. et al. |
| 7,333,002 B2 | 2/2008 | Bixler et al. |
| 7,336,187 B2 | 2/2008 | Hubbard, Jr. et al. |
| 8,598,995 B2 | 12/2013 | Schuman et al. |
| 9,299,242 B2 | 3/2016 | Schuman et al. |
| 9,361,021 B2 * | 6/2016 | Jordan .................. G06Q 10/10 |
| 9,517,035 B2 | 12/2016 | Schuman et al. |
| 9,955,926 B2 | 5/2018 | Schuman et al. |
| 10,307,113 B2 | 6/2019 | Schuman et al. |
| 10,638,983 B2 | 5/2020 | Schuman et al. |
| 2001/0044823 A1 | 11/2001 | Labounty et al. |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0032583 A1 | 3/2002 | Joao |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0101349 A1 | 8/2002 | Rojas, Jr. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0093300 A1 | 5/2003 | Denholm |
| 2003/0146835 A1 | 8/2003 | Carter |
| 2003/0149598 A1 | 8/2003 | Santoso et al. |
| 2003/0176798 A1 | 9/2003 | Simon |
| 2003/0179099 A1 | 9/2003 | Perea, Jr. et al. |
| 2003/0197614 A1 | 10/2003 | Smith et al. |
| 2003/0206116 A1 | 11/2003 | Weiner et al. |
| 2003/0212575 A1 | 11/2003 | Saalsaa et al. |
| 2003/0230469 A1 | 12/2003 | Engler |
| 2004/0064890 A1 | 4/2004 | Kim et al. |
| 2004/0158922 A1 | 8/2004 | Eberler et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0222897 A1 | 11/2004 | Schuhmann et al. |
| 2004/0243446 A1 | 12/2004 | Wyatt |
| 2004/0249670 A1 | 12/2004 | Noguchi et al. |
| 2004/0261184 A1 | 12/2004 | Flick |
| 2005/0035862 A1 | 2/2005 | Wildman et al. |
| 2005/0055779 A1 | 3/2005 | Damewood |
| 2005/0076441 A1 | 4/2005 | Dominati et al. |
| 2005/0110617 A1 | 5/2005 | Kile et al. |
| 2005/0155149 A1 | 7/2005 | Pedersen |
| 2005/0170863 A1 | 8/2005 | Shostak |
| 2005/0206505 A1 | 9/2005 | Arcaria |
| 2005/0242946 A1 | 11/2005 | Hubbard, Jr. et al. |
| 2006/0046579 A1 | 3/2006 | Karadimas et al. |
| 2006/0049936 A1 | 3/2006 | Collins, Jr. et al. |
| 2006/0114854 A1 | 6/2006 | Wotherspoon et al. |
| 2006/0126560 A1 | 6/2006 | Wotherspoon et al. |
| 2006/0136265 A1 | 6/2006 | Summers et al. |
| 2006/0214786 A1 | 9/2006 | Bixler et al. |
| 2006/0220798 A1 | 10/2006 | Willis |
| 2006/0239195 A1 | 10/2006 | Camins et al. |
| 2006/0248221 A1 | 11/2006 | Hottel et al. |
| 2006/0267740 A1 | 11/2006 | Bixler et al. |
| 2007/0071114 A1 | 3/2007 | Sanderford, Jr. et al. |
| 2007/0135688 A1 | 6/2007 | Brown |
| 2007/0156456 A1 | 7/2007 | McGillin et al. |
| 2007/0210917 A1 | 9/2007 | Collins, Jr. et al. |
| 2007/0229249 A1 | 10/2007 | McNeal et al. |
| 2007/0237487 A1 | 10/2007 | Lin |
| 2007/0239484 A1 | 10/2007 | Around et al. |
| 2007/0257788 A1 | 11/2007 | Carlson et al. |
| 2008/0004904 A1 | 1/2008 | Tran |
| 2008/0015900 A1 | 1/2008 | Denholm |
| 2008/0018436 A1 | 1/2008 | Traughber et al. |
| 2008/0027754 A1 | 1/2008 | Auker et al. |
| 2009/0212925 A1 | 8/2009 | Schuman, Sr. et al. |
| 2009/0212956 A1 | 8/2009 | Schuman et al. |
| 2009/0217080 A1 | 8/2009 | Ferguson et al. |
| 2016/0166214 A1 | 6/2016 | Schuman et al. |
| 2017/0049408 A1 | 2/2017 | Schuman et al. |
| 2018/0220974 A1 | 8/2018 | Schuman et al. |
| 2019/0254613 A1 | 8/2019 | Schuman et al. |

FOREIGN PATENT DOCUMENTS

| | | |
|---|---|---|
| EP | 1 679 648 | 7/2006 |
| GB | 250 769 | 4/1926 |
| JP | 1-76197 | 2/1989 |
| WO | WO 95/23378 | 8/1995 |
| WO | WO 98/08203 | 2/1998 |
| WO | 0198936 | 12/2001 |

(56) References Cited

FOREIGN PATENT DOCUMENTS

| WO | WO 01/93175 A2 | 12/2001 |
| WO | WO 02/091297 | 11/2002 |
| WO | WO 2004/036390 | 4/2004 |

OTHER PUBLICATIONS

Hill-Rom A Hillenbrand Industry, The COMposer Communication System Service Manual, 1995.
Hill-Rom A Hillenbrand Industry, COMLinx™ Enterprise Solutions Nurse Communication Module, User's Guide, 2000.
Partial European Search Report from EP 09 25 0420, dated Jun. 16, 2009.
European Search Report for European Patent Application No. 12164815.8, dated Mar. 9, 2012, 8 pages.
COMLinx Nurse Communication Module Technological Advances, Jul. 13, 2006, 4 pages.
European Search Report for EP 09 25 0419, dated Aug. 13, 2010, (7 pages).
European Search Report for European Patent Application No. 12164817.4, dated Mar. 9, 2012, 9 pages.
Notice of Allowance and Fee(s) Due, Part B—Fee(s) Transmittal, Determination of Patent Term Adjustment Under 35 U.S.C. 1.54(b) and Notice of Allowability for U.S. Appl. No. 12/369,832, dated Jan. 19, 2012, 7 pages.
European Search Report for European Patent Application No. 12164812.5, dated Mar. 9, 2012, 8 pages.
Extended European Search Report for European Patent Application No. 19197129.0 dated Oct. 15, 2019; 11 pages.
Communication from the European Patent Office for European Patent Application No. 17197129.0 dated Oct. 23, 2020 (6 pages).

\* cited by examiner

DISTRIBUTED HEALTHCARE COMMUNICATION SYSTEM

This application is a continuation of U.S. application Ser. No. 16/398,775, filed Apr. 30, 2019, issued as U.S. Pat. No. 10,638,983, which is a continuation of U.S. application Ser. No. 15/939,762, filed Mar. 29, 2018, issued as U.S. Pat. No. 10,307,113, which is a continuation of U.S. application Ser. No. 15/332,699, filed Oct. 24, 2016, issued as U.S. Pat. No. 9,955,926, which is a continuation of U.S. application Ser. No. 15/053,303, filed Feb. 25, 2016, issued as U.S. Pat. No. 9,517,035, which is a continuation of U.S. application Ser. No. 14/091,392, filed Nov. 27, 2013, issued as U.S. Pat. No. 9,299,242, which is a continuation of U.S. application Ser. No. 12/369,813, filed Feb. 12, 2009, issued as U.S. Pat. No. 8,598,995, and which claimed the benefit, under 35 U.S.C. § 119(e), of U.S. Provisional Patent Application Nos. 61/066,877, 61/066,882, 61/066,883, and 61/066,918, each of which was filed Feb. 22, 2008, and U.S. Provisional Patent Application No. 61/145,306, which was filed Jan. 16, 2009, the disclosures of all of which are hereby expressly incorporated by reference herein.

BACKGROUND

The present disclosure relates to healthcare communication systems, such as nurse call systems. In particular the present disclosure relates to healthcare communication systems having a master station and devices in patient rooms that communicate with the master station.

Most hospitals and other types of in-patient healthcare facilities have some sort of a nurse call system. Patients place nurse calls by pressing a nurse call button located on a hospital bed or on a hand-held unit, known in the art as a pillow speaker or pillow speaker unit, or by actuating a wall mounted switch. After a patient places a nurse call, a caregiver at a master station may answer the nurse call which enables voice communications between the caregiver at the master station and the patient. To facilitate such voice communications a microphone and speaker is located somewhere in the patient room. Oftentimes the microphone and speaker are included in the pillow speaker unit or in an audio station mounted to a wall of the patient room or to a headwall unit which, in turn, is mounted to a wall of the patient room.

One example of a known nurse call system is Hill-Rom's COMLINX® system. In addition to the voice communication function, the COMLINX system is connected to the patient's hospital bed to receive bed status information regarding various aspects of the hospital bed such as the position of the siderails of the bed (e.g., up or down), whether the bed's casters are braked or released, whether or not an upper frame of the bed is in its lowest position, and so forth. See, for example, U.S. Pat. Nos. 7,242,308; 6,897,780; 6,362,725; 6,147,592; 5,838,223; 5,699,038; and 5,561,412, which relate to the COMLINX system. Another example of a known nurse call system is G.E. Healthcare's TELLIGENCE™ system.

SUMMARY

The present invention comprises a healthcare communication system and/or method, or a component thereof, that has any one or more of the features listed in the appended claims and/or any one or more of the following features, which alone or in any combination may comprise patentable subject matter:

One or more graphical audio stations may be provided in one or more patient rooms. A master station may be communicatively coupled to the graphical audio stations. Optionally, one or more graphical audio stations may be provided outside the patient rooms, such as in one or more staff work areas. Staff work areas may include, for example, hallways or staff lounges. The graphical audio stations may each have a graphical display screen and user inputs, at least one of which is usable to establish a two-way communication link with a selected one of the other graphical audio stations. Thus, graphical audio stations in patient rooms can be used to establish two-way communications with graphical audio stations in other rooms to permit room-to-room communication by caregivers. At least one of the user inputs of the graphical audio stations may also be usable to establish a two-way communication link with one or more of the following: the master station, a wireless communication device carried by a caregiver, or a telephone of the healthcare facility.

The user inputs of the graphical audio stations may be displayed on the graphical display screen. Thus, the graphical display screen of the audio station may be a touch screen. The user inputs may be included as part of a user interface displayed on the display screen. In some contemplated embodiments, one or more of the user inputs may comprise buttons or keys spaced from the graphical display screen, such as being situated on a housing adjacent the graphical display screen. The graphical audio station may include a speaker and microphone. The graphical audio station may have a housing that carries the graphical display screen, the speaker, the microphone, and associated circuitry. However, this need not be the case and the speaker and microphone may be located in one or more devices other than the graphical audio station and be communicatively coupled to it either directly or via intervening circuitry.

The graphical audio stations located in the patient rooms may each be configured to receive a nurse call signal and to communicate the nurse call signal to the master station. The nurse call signal may be received from a hospital bed. The nurse call signal may be generated in response to a patient manipulating a nurse call input, such as a button or a switch, which is located on the hospital bed. Alternatively or additionally, the nurse call signal may be received from a hand-held pillow speaker unit or from a wall-mounted call unit having a switch, cord, lever, button, or other user input, which is moved or otherwise actuated to initiate the nurse call signal.

The healthcare communication system may further comprise a plurality of dome light assemblies. Each dome light assembly may be located in a hallway near a door of a respective patient room. The nurse call signal may be communicated to the master station via a circuit board located in a housing mounted near a respective dome light assembly. Thus, the two-way communication link may include the circuit board located near a respective dome light assembly. The healthcare communication system may also include a plurality of bed connector units, each of which may be coupled to a respective hospital bed and to either a respective graphical audio station or a respective circuit board located near a respective dome light assembly. One or more bed connector units may be integrated with a graphical audio station. A Power over Ethernet (PoE) switch may also be included in the healthcare communication system and may be coupled to the master station and to the circuit boards of various dome light assemblies. The two-way communication links between the master station and various graphical audio stations may, therefore, include the Power over Ethernet switch.

Each of the graphical audio stations may be configured to receive an alert signal from at least one piece of equipment located in the respective hospital room. The at least one piece of equipment may comprise a hospital bed, for example. Alternatively or additionally, alerts from other types of equipment, such as IV pumps, ventilators, and patient monitors of all types including EKG's, EEG's, blood pressure monitors, and pulse oximeters, for example, may be received by the graphical audio station and communicated to the master and/or to other devices such as other graphical audio stations and portable devices that are carried by one or more caregivers and that have wireless communication capability. The alert signal may correspond to an alarm condition of the at least one piece of equipment or the alert signal may correspond to a non-alarm condition or the alert may be a reminder or message set up by the caregiver or automatically generated by the piece of equipment.

At least one of the user inputs of the plurality of graphical audio stations may be usable to send a one-way voice page to a subset of the plurality of graphical audio stations. At least one of the user inputs of the plurality of graphical audio stations may be usable to select the subset of graphical audio stations to which the one-way voice page is to be sent. The voice page may also be sent to the master station if the master station is selected using the user inputs of the graphical audio station, or if the master station is among the devices in a group of devices selected using the user inputs. Alternatively or additionally, the graphical audio stations may be usable to send a one-page to a pre-selected or pre-determined subset of the graphical audio stations, along with one or more master stations and/or one or more staff stations and/or one or more other types of communication devices such as telephones or wireless communication devices, including cellular telephones, that are included in the subset.

At least one of the user inputs of the graphical audio stations may be usable to send a text message to a wireless device carried by a caregiver. At least one of the user inputs of the plurality of graphical audio stations may be usable to browse web pages hosted on servers of the healthcare facility or that are accessible via the Internet. At least one of the user inputs of the plurality of graphical audio stations may be usable to view multimedia content, such as videos, which are hosted on at least one server of the healthcare facility or which are accessible via the Internet. The videos may be, for example, educational videos regarding pieces of equipment being used to care for the patient or regarding medical procedures or regarding some other topic. At least one of the user inputs of the plurality of graphical audio stations may be usable to perform at least one of the following functions: view alerts or nurse calls, acknowledge alerts or nurse calls, answer alerts or nurse calls, and cancel alerts or nurse calls, including nurse calls and alerts originating in other patient rooms.

The master station may comprise a graphical display screen and a telephone handset. Master station user inputs may be displayed on the graphical display screen of the master station. At least one of the master station user inputs may be usable to initiate a two-way communication link from the master station to at least one of the following: at least one of the plurality of graphical audio stations, a wireless communication device carried by a caregiver, and a telephone of the healthcare facility. By presenting the master station user inputs on the graphical display screen, other alphanumeric inputs, such as phone keypads and computer keyboards, may be omitted from the master station. The master station may sometimes be referred to herein as a master console or primary console.

The healthcare communication system may also have an input/output circuit spaced from the graphical audio stations. At least some of the graphical audio stations may communicate with the input/output circuit according to a first communication protocol and the input/output circuit may communicate with the master station according to a second communication protocol, such as a TCP/IP protocol, for example. The plurality of graphical audio stations and the master station may be configured to comply with the Underwriter's Laboratories (UL) 1069 standard which relates to Hospital Signaling and Nurse Call Equipment.

According to this disclosure, the graphical audio station is among the types of devices that may be referred to as a computer device. Thus, this disclosure contemplates that a computer device located in a patient room of a healthcare facility may be communicatively coupled to the master station, may be configured to receive a nurse call signal and/or an alert signal from a piece of equipment located in the patient room, may have a graphical display screen operable to display at least one user interface, and may be configured to perform one or more of the following functions in response to use of the at least one user interface: establish a two-way voice communication link with the master station; establish a two-way voice communication link with another computer device in another patient room; establish a two-way voice communication link with a computer device located in a staff work area; establish a two-way voice communication link with a wireless communication device carried by caregiver; establish a two-way voice communication link with a telephone of the healthcare facility; broadcast a voice page to a group of other computer devices; select a set of computer devices to which a voice page is to be communicated; send a text message to a portable device that is carried by a caregiver and that has wireless communication capability; compose a text message to be sent to a portable device that is carried by a caregiver and that has wireless communication capability; browse web pages hosted on servers of the healthcare facility; browse web pages accessible via the Internet; view multimedia content, such as videos, hosted on servers of the healthcare facility; view multimedia content accessible via the Internet; view a list of alerts or nurse calls originating in other patient rooms; acknowledge alerts or nurse calls originating in other patient rooms; answer alerts or nurse calls originating in other patient rooms; or cancel alerts or nurse calls originating in other patient rooms.

The computer device may also be configured to automatically perform one or more of the following functions: communicate the nurse call and/or alert signal to the master station; communicate information about the nurse call and/or alert signal to the master station; or process the nurse call and/or alert signal and communicate a processed signal to the master station. The healthcare communication system may have many such computer devices, some of which are located in patient rooms and at least one of which is located in a staff area. The computer devices and the master station may be configured to comply with the UL 1069 standard so as to provide a healthcare facility with a nurse call system.

To create a master station or console, the graphical audio station may be mounted to a base unit which has a telephone handset. The graphical audio stations may also include locating receiver circuitry which receives wireless signals from portable transmitters carried or worn by caregivers to track the whereabouts of the caregivers throughout the healthcare facility. When the receiver circuitry of the graphical audio stations sense the presence of a caregiver, by receiving the wireless signal from the caregiver's associated transmitter, the graphical audio station may turn on a back light and display a particular screen. The master station may be configured to be coupled to the network of the healthcare facility. The graphical audio stations may link to the network of the healthcare facility through the master station.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
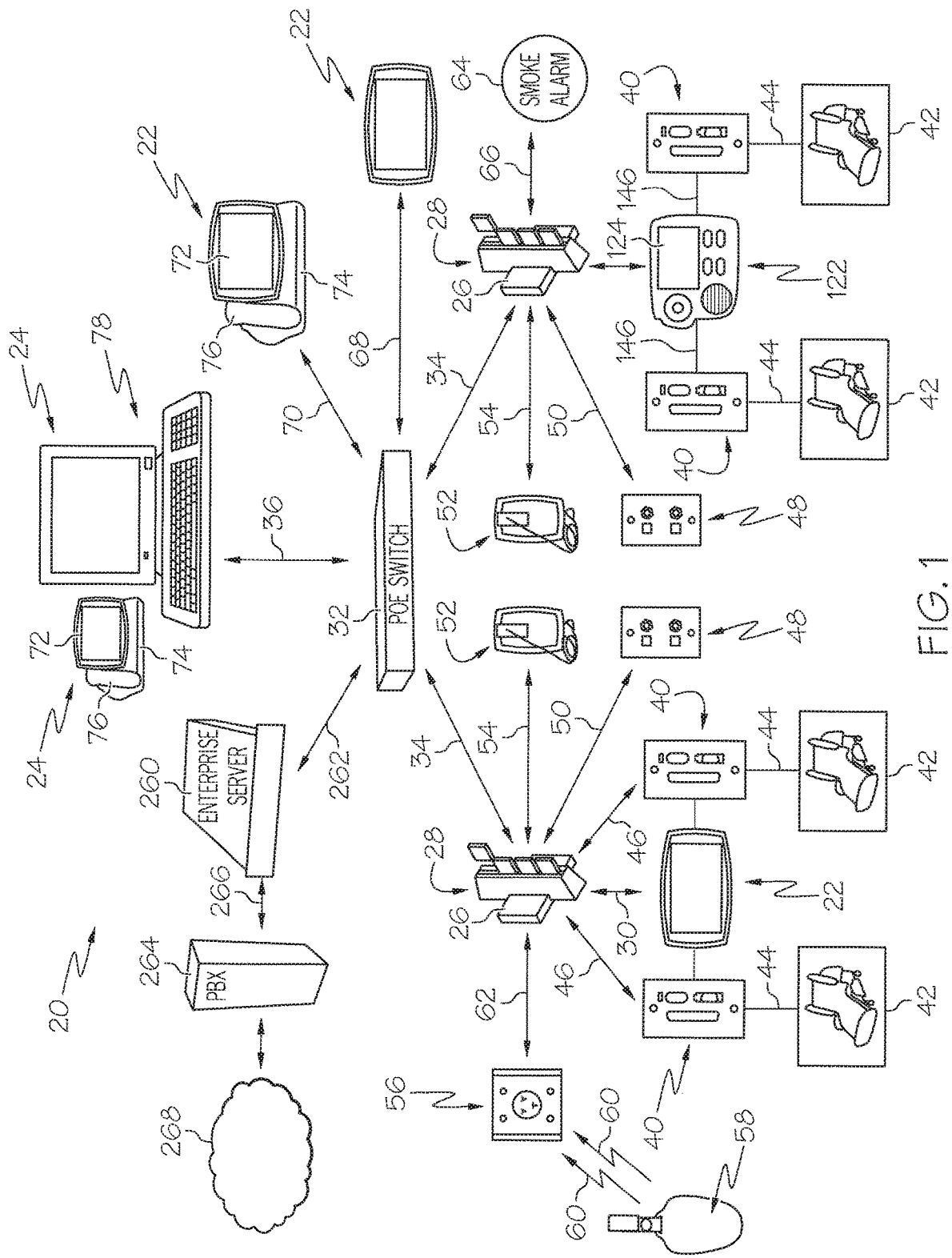
FIG. 1 is a block diagram showing various components of a nurse call system, some of which are included as a part of a healthcare communication system according to this disclosure.

A healthcare communication system 20 includes a plurality of graphical audio stations 22 and a master station or console 24 which are communicatively coupled as shown diagrammatically in FIG. 1. Many of the stations 22 are located in patient rooms and are mounted, for example, to a wall of the respective room or to a headwall unit that, in turn, is mounted to a wall of the respective room. Stations 22 may be mounted to other architectural support structures, such as service chases or columns just to name a couple. Stations 22 may be located in other areas of the healthcare facility as well, such as in staff work areas including, for example, hallways and staff lounges. The stations 22 located in patient rooms may sometimes be referred to herein as patient stations 22, whereas the stations 22 located in staff work areas may be sometimes be referred to herein as staff stations 22. The functionality of stations 22 described herein is applicable to all stations 22 regardless of whether the station 22 is a patient station 22 or a staff station 22, unless specifically noted otherwise.

Patient stations 22 communicate bidirectionally (e.g., two-way communication) with an input/output (I/O) circuit 27 which is located within a housing 26 mounted near a dome light assembly 28. The bidirectional communication is indicated diagrammatically in FIG. 1 by double headed arrow 30. I/O circuit 27 is also shown diagrammatically in FIG. 2. Dome light assemblies 28 are typically mounted outside respective patient rooms near the doorways of the rooms and are readily visible to caregivers in the hallway to determine whether any calls or other events indicated on the dome light are occurring within the associated room. Thus, housings 26 with I/O circuit 27 therein are mounted generally at these same locations outside patient rooms. Additional details of the dome light assemblies 28, housing 26, and circuit board 27 are provided in U.S. Provisional Patent Application No. 61/066,883 which was filed Feb. 22, 2008, which was titled "Indicator Assembly for Healthcare Communication System," and which is already incorporated by reference herein.

A 9-page electric circuit schematic illustrating one possible electric circuit implementation of one embodiment of the circuitry of dome light assembly 28 is shown in FIG. 12 of U.S. Provisional Patent Application No. 61/066,877, which was filed Feb. 22, 2008, which was titled "Distributed Healthcare Communication System," and which is already incorporated by reference herein. In one embodiment, dome light assembly 28 is, for example, an International Business Machines (IBM) Part No. 43T1899 dome light fixture. A 55-page electric circuit schematic illustrating one possible electric circuit implementation of input/output (I/O) circuit 27 according to this disclosure is shown in FIG. 15 of U.S. Provisional Patent Application No. 61/066,877 which is already incorporated by reference herein. In one embodiment, I/O circuit 27 is, for example, an IBM part no. 43T2063 IO Board. In some Appendices of the written description of U.S. Provisional Patent Application No. 61/066,877, I/O circuit 27 may be referred to as an I/O board or an I/O circuit board. However, this is not to imply that all circuit components of the circuitry of I/O circuit 27 need to be on a single circuit board, but that is certainly one possibility. Thus, in some contemplated embodiments I/O circuitry 27 may be distributed among numerous circuit boards, and in other contemplated embodiments some or all of the components of circuit 27 may not be on any circuit board at all. While illustrative circuit 27 is located in housing 26, it is within the scope of this disclosure for various components of circuit 27 to be located in separate housings.

The I/O circuit 27 of assembly 28 communicates bidirectionally with a Power over Ethernet (PoE) switch 32 as indicated diagrammatically in FIG. 1 by double headed arrow 34. PoE switch 32 communicates bidirectionally with master station 24 as indicated diagrammatically by double headed arrow 36. Suitable PoE switches are available from a variety of suppliers and may include, for example, the PoE switch marketed by Hill-Rom Company, Inc. in connection with its NaviCare® Nurse Call™ system or such as one or more of the various Dell PoE switches marketed under the PowerConnect™ brand name. Optionally, an external power supply is coupled to PoE switch 32 to provide back up power to PoE switch 32 in the event that an internal power supply of PoE switch 32 fails. One example of a suitable external power supply is Optimal Power part number OPN300-48SN which is coupled to the PoE switch 32 using an Optimal Power part number OPNC30148 cable. While only one patient station 22 is shown in FIG. 1 as being communicatively coupled to master station 24, via the I/O circuit board 27 of assembly 28 and via PoE switch 32, it will be appreciated that system 20 may have numerous such patient stations 22 that may communicate with master station 24 via respective I/O circuit boards 27 and via PoE switch 32.

Typically, all of the patient stations 22 of a nursing unit communicate with the same master station 24. The master stations 24 and graphical audio stations 22 of different nursing units may be coupled together by interconnecting the respective PoE switches as indicated diagrammatically in FIG. 3 via dotted lines 38. In this way, information can be shared, and communications established, between computers devices, such as stations 22, of different nursing units. This is an improvement over prior art systems having the master stations and audio stations of each nursing unit isolated and unable to communicate with the master stations and audio stations of other nursing units.

Figure 2:
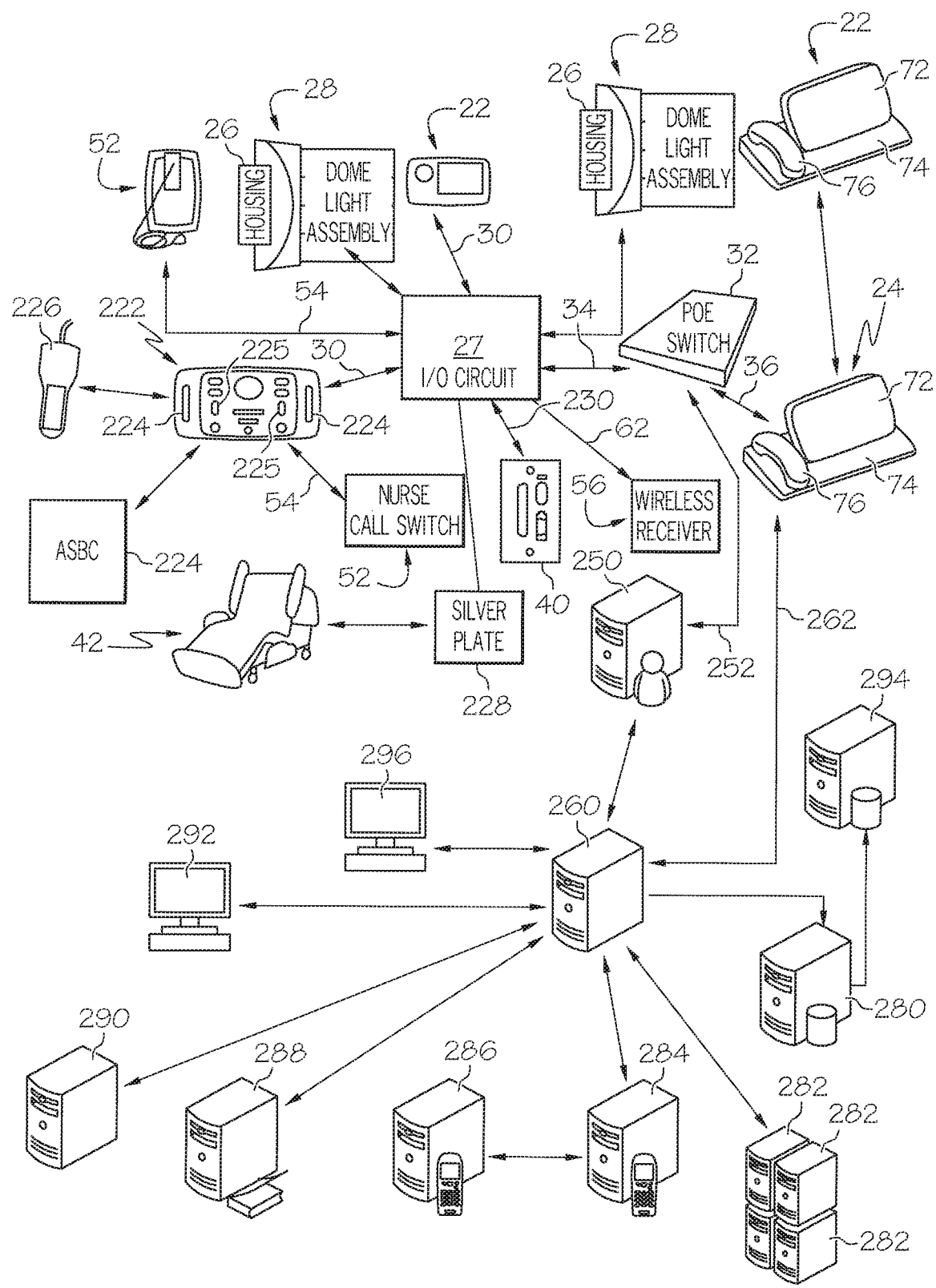
FIG. 2 is a block diagram showing a master console of the nurse call system coupling the nurse call system to other computer devices included in a computer network of the healthcare facility.

In some embodiments, such as the one shown in FIG. 1, system 20 includes bed connector units 40, each of which is communicatively coupled to an associated hospital bed 42 as shown diagrammatically in FIG. 1 via lines 44. Bed connector units 40 are, in turn coupled to a respective circuit board 27 as indicated diagrammatically in FIG. 1 via lines 46. In some other embodiments, bed connector units 22 may be coupled to graphical audio station 22 which communicates with the corresponding circuit board 27 in the way that bed connector units 40 are shown coupling to graphical audio stations 124 (discussed in further detail below) via diagrammatic lines 146 in FIG. 1. In still other embodiments, bed connectors units 40 may be integrated into a common housing of graphical audio stations 22 (and stations 124 as well) in the way that connectors 224, 225 are integrated into standard audio station 222 as shown in FIG. 2. Stations 222 are discussed in further detail below.

One version of bed connector unit 40 is referred to in some of the Appendices of the written description of U.S. Provisional Patent Application No. 61/066,877 as a Bed Interface Unit (BIU) which, in one embodiment, includes a 37-pin connector to attach to a bed cable, includes another connector for attachment of a call pendant or pillow speaker unit, and an includes a button that can be manually pressed to send and/or cancel a nurse call. Another version of a bed connector 228 is referred to as a Silver Plate in some of the Appendices attached in U.S. Provisional Patent Application No. 61/066,877 and is shown in FIG. 2. Bed connector 228 is a low cost connector which includes only a connector to which bed 42 couples via a suitable connection cord. In some embodiments, beds 42 comprise one or more of the beds marketed by Hill-Rom Company, Inc. under the brand names TOTALCARE®, VERSACARE®, ADVANCED-1000™, CCUII™ and ADVANTA™.

Many other types of devices in a patient room may also couple to a respective I/O circuit 27 mounted near the corresponding dome light assembly 28 to communicate with master station 24 and, if desired, other computer devices of the a computer network of the healthcare facility. For example, in FIG. 1, an equipment connector 48 to which patient care equipment, such as patient monitoring equipment, may be connected is coupled to the I/O circuit 27 as indicated diagrammatically by double-headed arrow 50 and a wall-mounted nurse call switch 52 which may be mounted in a lavatory of the patient room, for example, is coupled to the circuit board 27 of assembly 28 as indicated diagrammatically by double-headed arrow 54. Furthermore, a wireless receiver 56, which illustratively is an infrared receiver that receives wireless signals 60 from locating-and-tracking badges 58 worn or carried by caregivers is coupled to the I/O circuit 27 of assembly 28 as indicated diagrammatically by double-headed arrow 62. It is also contemplated herein that a smoke alarm 64 is coupleable to the I/O circuit 27 of assembly 28 as indicated in FIG. 1 by double headed arrow 66.

As previously mentioned, some graphical audio stations 22 are located in staff work areas and are referred to as staff stations or consoles 22. In FIG. 1, a first staff station 22 communicates bidirectionally with PoE switch 32 via a communications link 68 and a second staff station 22 communicates bidirectionally with PoE switch 32 via a communications link 70. The first staff station 22 is mounted to a wall, for example, whereas the second staff station 22 has a graphical display screen module 72 connected to a base module 74 which includes a telephone hand set 76. The master station 24 shown in the FIG. 1 example also has a graphical display screen module 72 connected to a base module 74 which has a telephone handset 76. The FIG. 1 example also shows a personal computer 78 which cooperates with the associated display screen module 72 to provide the master station functionality. In other embodiments, personal computer 78 is the only computer device included in master station 24 while, in still other embodiments, personal computer 78 is omitted. Thus, depending upon the manner in which a graphical display module 72 is programmed it can serve as a patient station 22, a staff station 22 or as a master station 24. When serving as a staff station 22 or a master station 24, module 72 can be coupled to base module 74, if desired. The display screen of module 72 is approximately a 10 inch display screen in some embodiments and therefore is larger than the LCD screen used in, for example, the COMLINX® system.

Each of the communications links 30, 34, 36, 44, 46, 50, 54, 60, 62, 66 shown diagrammatically by lines or arrows in FIG. 1 may include wired links and/or wireless links and/or combinations thereof, along with associated connectors. For example, with regard to links 44 between beds 42 and bed connector units 40, known cables having 37-pin connectors (or similar connectors) may provide these links 44. Alternatively or additionally, some of links 44 may be wireless links, in which case, the respective beds 42 and units 40 have appropriate wireless transmitter and wireless receiver circuitry, which may be in the form of a wireless transceiver. Such wireless communication between beds 42 and units 40 is discussed, for example, in U.S. Pat. No. 7,319,386 and in U.S. Patent Application Publication No. 2007/0210917 A1, both of which are hereby incorporated herein by this reference.

While this disclosure contemplates that the data formatting for the data transmitted over any of links 30, 34, 36, 44, 46, 50, 54, 60, 62, 66, 68, 70 may be according to any suitable data formatting protocol, in one embodiment, the data formatting protocol is according to the protocol discussed in detail in the "Project NCM II, Interface Design Specification, NPD05514" document which is attached to U.S. Provisional Patent Application No. 61/066,877 as Appendix 1 and which is considered part of the written description of that provisional patent application and of this patent application via the incorporation by reference previously made in this application of U.S. Provisional Patent Application No. 61/066,877. In general, the protocol described in Appendix 1 of U.S. Provisional Patent Application No. 61/066,877 uses extensible markup language (XML) strings to transfer data. This protocol is sometimes referred to as the Palmetto Protocol and is sometimes referred to as the XML protocol herein and in some of the documents in the Appendices of the written description of U.S. Provisional Patent Application No. 61/066,877. It is also contemplated that the communication protocol for links 30, 34, 36, 44, 46, 50, 54, 60, 62, 66 may be according to any suitable protocol such as the TCP/IP protocol, the RS-232 protocol, the RS-422 protocol, the RS-423 protocol, or the RS-485 protocol, or similar such protocols, and such as wireless protocols including any of the IEEE 802.11 protocols (where x represents the various revision levels a, b, c, d, e, g and so forth of the 802.11 protocol), the Bluetooth protocol, the Zigbee protocol, or similar such wireless communication protocols.

In one embodiment, links 44, 46, 54, 62, which are the communications links associated with a patient room that communicate between devices in the patient room and the I/O circuit board of dome light assembly 28, are according to the RS-485 protocol, whereas links 34, 36, 68, 70, which are the links to and from PoE switch 32, are according to the TCP/IP protocol. The devices that communicate over these various links are configured and programmed appropriately for the required RS-485 or TCP/IP protocol, as the case may be.

It should be noted that, in one contemplated embodiment, link 30 comprises a coupler that couples to a PoE port of the respective I/O circuit 27 such that communications over link 30 are transmitted according to the TCP/IP protocol and I/O circuit 27 provides feed through of any data, including communication data such as voice data, communicated between station 22 and PoE switch 32. Because stations 22 communicate according to the TCP/IP protocol, staff stations 22 are coupleable to PoE switch 32 without the use of an intervening I/O circuit 27, if desired. As to the various devices coupled to I/O circuit 27 other than station 22, the circuitry of I/O circuit 27 operates to convert the data from these various devices according to their device-specific communication protocols (e.g., serial links to stations 122, 222; locating and tracking receiver 56 room bus protocol; bed connector 40 room bus protocol; and serial to dome light protocol) into the TCP/IP protocol for subsequent transmission to the PoE switch and ultimately to the master station 24 and beyond, if desired.

According to this disclosure, system 20 is scaleable such that basic, intermediate, and advanced nurse call systems can be created depending upon the particular requirements of a particular healthcare facility. The graphical audio stations 22 discussed herein are associated with an advanced nurse call system and are referred to in several of the documents of the Appendices of U.S. Provisional Patent Application No. 61/066,877, which are considered part of this written description via incorporation by reference, as an advanced graphical audio station (AGAS) and are referred to in the documents of the Appendices of U.S. Provisional Patent Application No. 61/145,306, which is also considered part of this written description via incorporation by reference, as a Graphical Room Station 10 (GRS-10). A 42-page electric circuit schematic illustrating one possible electric circuit implementation of one embodiment of an advanced graphical audio station (AGAS) 22 according to this disclosure is shown in FIG. 11 of U.S. Provisional Patent Application No. 61/066,877. In one embodiment, audio graphical station 22 is an IBM part no. 43T2058 station.

A graphical audio station 122, shown in FIG. 1, provides mid-range or intermediate functionality and includes a smaller graphical display screen 124 than the display screen of stations 22. This type of intermediate station 122 referred to in the documents of the Appendices of U.S. Provisional Patent Application No. 61/066,877 as a graphical audio station (GAS) and in the documents of the Appendices of U.S. Provisional Patent Application No. 61/145,306 as a Graphical Room Station 5 (GRS-5). FIGS. 13 and 14 of U.S. Provisional Patent Application No. 61/066,877 cooperate to provide an electric circuit schematic illustrating one possible electric circuit implementation of one embodiment of graphical audio station (GAS) 122. Graphical audio station 122 in one embodiment comprises IBM part nos. 43T2071 and 43T2067.

A standard audio station 222, shown in FIG. 2 and referred to in the documents of the Appendices of U.S. Provisional Patent Application No. 61/066,877 as a standard audio station (SAS) and referred to in the Appendices of U.S. Provisional Patent Application No. 61/145,306 as Standard Room Station (SRS) has no graphical display screen. A 20-page electric circuit schematic illustrating one possible electric circuit implementation of one embodiment of standard audio station 222 is shown in FIG. 16 of U.S. Provisional Patent Application No. 61/066,877. Graphical audio station 222 in one embodiment comprises IBM part no. 43T2082. Additional details of stations 22, 24, 122, 222 are provided in a U.S. Provisional Patent Application No. 61/066,882 which was filed Feb. 22, 2008, which is titled "User Station for Healthcare Communication System," and which is already incorporated by reference herein.

Standard audio stations 222 are a low cost offering that provides call cancel, call placement, reception for signals from badges 58, and voice communication functionality. As mentioned already, stations 222 do not have a graphical display. Stations 222 connect to the I/O circuit board of assembly 28 via an RS-485 connection 30. Stations 222 can be configured as a patient station, staff station, or visitor station. As indicated in FIG. 2, beds 42 may couple to stations 222 via an audio station bed connector (ASIC) 224. Also, pillow speaker units 226 and/or a call switch 52 (e.g., a call cord in some instances) may couple to station 222, such as by coupling to a connector 225 included as part of station 222. It is contemplated that bed connector 224 can be integrated into station 22 and thus, in FIG. 2, reference numeral 224 is used to denote such an integrated connector 224 of station 222 as well as the separate bed connector block 224. In the FIG. 2 example, however, bed 42 is coupled to a Silver Plate 228 which is, in turn, coupled to the associated I/O board 27. The term "Silver" refers to the general color of the plate, not its material.

While FIG. 2 shows one block representative of I/O circuit 27 and shows two separate dome light assemblies 28 linked to it via unnumbered double-headed arrows, it should be appreciated that in some embodiments each assembly 28 has its own I/O circuit 27 as discussed previously. However, this need not be the case in all instances and therefore, having I/O circuits 27 located elsewhere in system 20 is within the scope of this disclosure. As further shown in FIG. 2, bed connector 40 is coupled to I/O circuit board 27 via an RS-485 communications link 230. FIG. 2 also shows station 22 coupled to I/O circuit 27 via link 30, PoE switch coupled to I/O circuit 27 via link 34, nurse call switch 52 coupled to I/O circuit 27 via link 54, a wireless receiver 56 coupled to I/O circuit 27 via link 62, and PoE switch 32 coupled to master station 24 via link 36. A staff station 22 is also shown in FIG. 2 in communication with master station 22 via link 70. While link 70 is shown directly between master console 24 and staff console 22, this is intended to be representative of a "logical link" to indicate that staff stations 22 communicate all received commands to the master station 24 and receive information about all other devices, such as patient stations 22, of the nursing unit from master station 24. Thus, staff stations 22 communicate with master station 24 via PoE switch 32.

Intermediate level audio stations 122 are a mid range offering that provides all of the functionality that a standard audio station 222 provides. In addition, stations 122 have small touch screen displays 124 that allow for monitoring calls, monitoring other types of alerts, view the location of staff, call located staff, change bed status (e.g., clean or dirty status), enable and disable nurse calls and alerts for a location or for a nursing unit. Unlike station 222, station 122 runs a Linux operating system (OS) that drives the graphical display and responds to user interaction. The content for display 124 of station 122 is controlled by the associated I/O circuit board 27 and by advanced services which are resident on other computer devices of system 20 as will be further discussed below. For base functionality, the I/O circuit controls the display of station 122 by sending XML strings to station 122. The circuitry of station 122 interprets those strings and displays a corresponding user interface (UI). If an advanced functionality is requested by station 122, the I/O circuit forwards the request for the advanced service(s) and the computer device of system 20 having the advanced service(s) replies back with the content in the appropriately formatted XML string.

In the illustrative example, advanced level audio stations 22, 24 provide all of the functionality of stations 122 except stations 22 couple to bed connectors 40, 224 via I/O circuits and not directly. However, in other embodiments contemplated herein, either of connectors 40, 224 may be integrated into station 22 or connected thereto in a manner similar to which they are integrated or connected in stations 122, 222 as described above. Stations 22, 24 also run a Linux OS, but it is written in C# programming code and executed under Mono, an open source implementation of the .NET framework maintained by Novell. This permits some code sharing between base and advanced systems as discussed in more detail below, an in the Appendices U.S. Provisional Patent Application No. 61/066,877, and as discussed in further detail in a U.S. Patent Application No. 61/066,918 which was filed Feb. 22, 2008, which is titled "Distributed Fault Tolerant Architecture for a Healthcare Communication System," and which is already incorporated by reference herein.

In broad general terms, it is the stations 22, 24 which are configured to communicate with various other computer devices, such as servers, included in the Ethernet of a healthcare facilities' system 20 and it is this additional communication capability that distinguishes these devices as advanced graphical audio stations. According to this disclosure, the components of system 20 which cooperate to provide a healthcare facility with a nurse call system are referred to collectively as a "base nurse call system." Thus, stations 22, 122, 222 and I/O circuit 27, dome light assemblies 28, and any of the equipment described above that is capable of providing a nurse call signal, as well as the associated master station 24 and PoE switch 32 along with any of the communication links interconnecting these components, are among the components which comprise a "base nurse call system" according to this disclosure. Staff stations 22, if present, are also considered to comprise part of the base nurse call system.

If voice communication capability among stations 22, 24, 122, 222 is to be a function of the nurse call system, then a Voice over Internet Protocol (VoIP) sever 250 is also included in the base nurse call system and is coupled to PoE switch 32 via a TCP/IP communications link 252 as shown in FIG. 2. Server 250 facilitates communication between which ever of stations 22, 24, 122, 222 are present in the system 20. Server 250 is configured to translate system operations and communications to the corresponding messages that then control endpoint devices, such as stations 22, 122, consoles 24, or room input/output circuits 27. As such, server 250 includes a soft telephony switch and other associated components. Server 250 may also provide integration with the hospital telecommunications structure (e.g., PBX or other voice communication system), although some other server may do so as well as is discussed below. In the illustrated embodiment, server 250 is a Windows server running 3CX. The components of the base nurse call system of illustrative system 20 are compliant with Underwriter's Laboratories 1069 standard according to this disclosure. This is not to imply that these components may not also be compliant with other standards relating to nurse call systems or relating to some other aspect of these devices.

According to this disclosure, stations 22, 24 also permit users to perform functions associated with an "advanced services system." The software code, such as applets or plug-ins, that provides stations 22 with these advanced functions may be communicated from various servers, or similar such computer devices discussed below, to stations 22 via stations 24, PoE switch 32, I/O boards 27, and the associated links 30, 34, 36. Thus, stations 22, 24 are dependent upon some devices that are not part of the base nurse call system, but instead are part of the advanced services system, to provide the advanced functionality to stations 22, 24. However, if these other devices are inoperable or communications with such devices of the advanced services system cannot be established or is otherwise faulty, the base nurse call system functionality is still able to operate. Thus, functionally, the base nurse call system is isolated from the advanced services system from a hardware standpoint and from a software standpoint.

Figure 3:
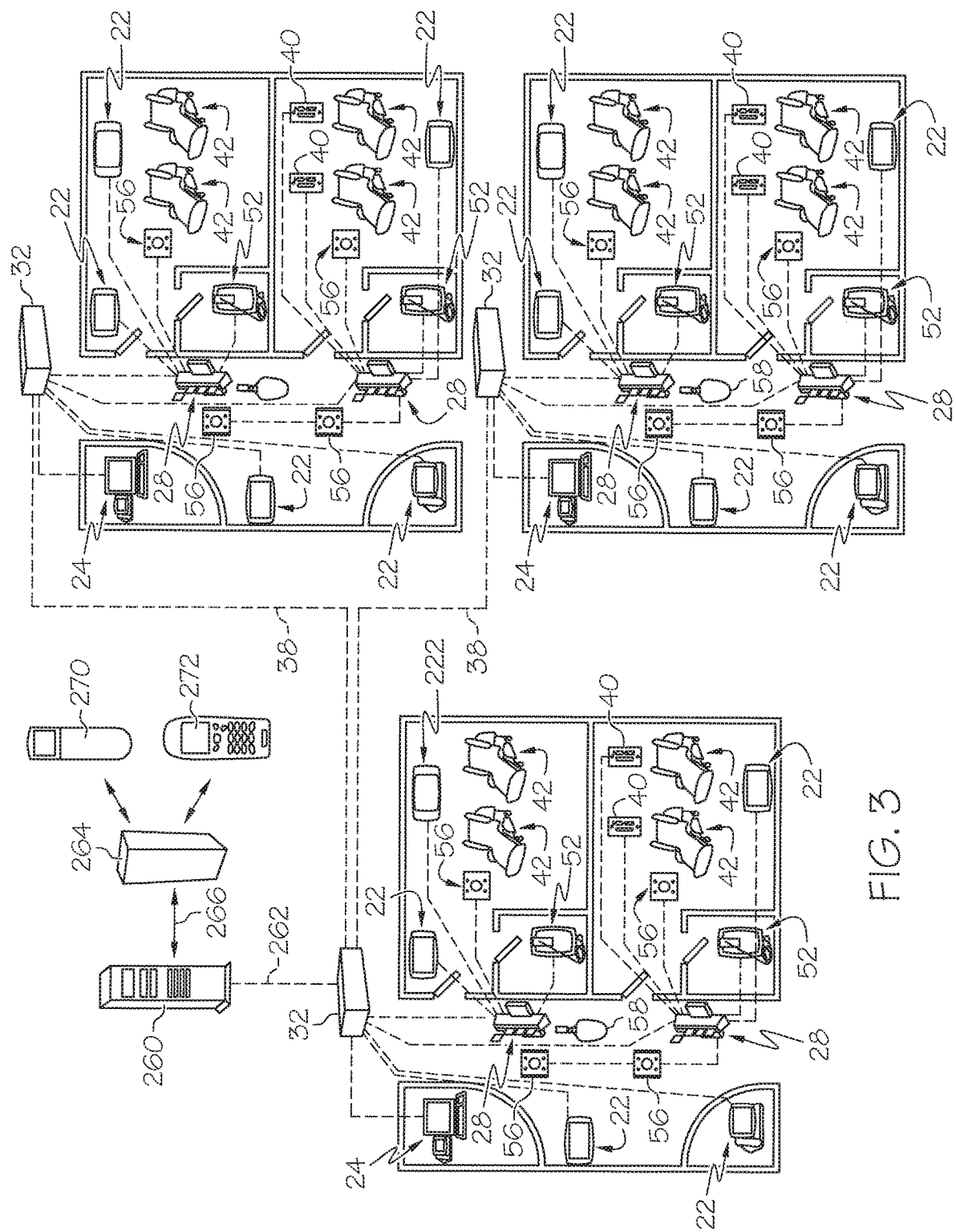
FIG. 3 is block diagram showing nurse call systems of various nursing units of a healthcare facility coupled to each other and coupled to other computer devices of the healthcare facility.

System 20 includes an enterprise server 260 which is included as part of the advanced services system as shown in FIGS. 1-3. Server 260 links to the nurse call portion of system 20 to provide advanced services thereto. A communication link 262 exists between server 260 and master station 24 via an appropriate switch device, such as a PoE switch 32 or other type of switch. Multiple master stations 24 may connect to server 260 via a switch 32 as shown in FIG. 3. As shown in FIG. 1, a private branch exchange (PBX) 264 may be coupled to server 260 via a VoIP communications link 266 to permit two-way voice calls to be placed over the public switched telephone network (PSTN) 268 to telephones outside the healthcare facility from graphical audio stations 22, 24, 122 by appropriate use of user inputs of user interfaces displayed on stations 22, 24, 122 as part of an associated advanced service. Two-way voice calls may be made similarly via server 260 and PBX 264 to wireless voice communication devices, such as a wireless communication badge 270 (e.g., a Vocera™ badge) or a wireless hand set 272, shown in FIG. 3, in response to appropriate use of the user interfaces of stations 22, 24, 122. Text messages may be sent to devices both inside and outside the healthcare facility via these same communications links in response to use of the user interfaces of stations 22, 24, 122. PSTN 268 is intended to represent, diagrammatically, a variety of telecommunication devices, including analog and digital devices, fixed telephones and mobile or cellular devices, personal data assistants (PDAs), pagers and the like.

As shown in FIG. 2, a non-exhaustive list of examples of other computer devices, each of which is optional according to this disclosure, that communicate via appropriate communications links with enterprise server 260 and therefore, with associated master stations 24 of one or more nurse call systems, include a database server 280; one or more third party servers 282; a first wireless communications server 284 for managing communications to and from wireless telecommunications devices; a second wireless communications server 286 for handling communications to and from other devices such as wireless badges for locating and tracking of staff members; a user authentication server 288 for managing user accounts, passwords, and user authorization; a workflow server 290, which facilitates integration with workflow software systems; a hospital administrative client 292 for conducting administrative tasks relating to patients and staff, such as adding patients and assigning staff to patients; and a status or reports server 294 for managing displays and reports of calls and notifications for one or more locations in the facility. An electronic status board 296 may also be coupled to server 260 as shown diagrammatically in FIG. 2. Status board 296 is operable to display locations within the facility and current information about them, such as active calls, bed status information, staff located in the healthcare facility, and staff assigned to the location.

While the term "server" is used herein, it will be understood by those skilled in the art that the functionality represented or performed by devices referred to as "severs" may comprise and be performed by any suitable computer device having software programs or services that may be resident and/or executable by any computer, device or equipment in the system or more than one computer, device or equipment in the network. Thus, there term "server" is intended to broadly encompass any computer device that is capable of performing the mentioned functions.

In the illustrated embodiment, server 284 is configured to provide communication and configuration for wireless devices using Emergin Wireless Office; server 286 is configured to provide communication and configuration for wireless Vocera devices; server 290 is configured to interface with or be included as part of a Hill-Rom® NaviCare™ system to receive and process task assignment and completion information. Plug-ins or applets or similar such software code may be resident on any of servers 260, 282, 284, 286, 288, 290, 292, 294, for example, and be retrieved by stations 22, 24 via server 260 as part of the "advanced services system" functionality. The software to display a particular user interface associated with an advanced service on a particular station 22, 24 which is operated by a user in a manner resulting in the request of the advance service may be executed on a device other than the one that requested it. For example, such advance service software may be executed by the circuitry of a master station 24 or I/O circuit 27, but yet the resulting user interface is display on one of stations 22. Additional details of the advanced services functionality are shown and described in the "Code Blue Advanced System Software, Architectural Design Specification, NPD05503" document attached to U.S. Provisional Patent Application No. 61/066,877 as Appendix 2 and is considered part of the written description of this patent application via incorporation by referenced of U.S. Provisional Patent Application No. 61/066,877. Still more details of system 20 and its "advanced services system" functionality is provided in a U.S. Provisional Patent Application No. 61/066,918 which is already incorporated by reference herein.

Referring now to FIGS. 4-10, examples of user interfaces which may appear on the graphical display screens of stations 22, 24 and, if appropriately programmed and configured on stations 122. The description below will discuss the various screens as appearing on one of stations 22. However, it should be understood that the discussion is applicable to the screens of stations 24 and, possibly, stations 122 in some embodiments. The Appendices of U.S. Provisional Patent Application No. 61/066,877 include a whole host of additional and alternative screen shot examples which are illustrative of the wide variety of functions that caregivers can perform by use of the multitude of user interfaces which are displayed on the display screens of stations 22, 24, 122 in connection with the operation of these device as part of a base nurse call system and when used as part of the advance services system.

Figure 4:
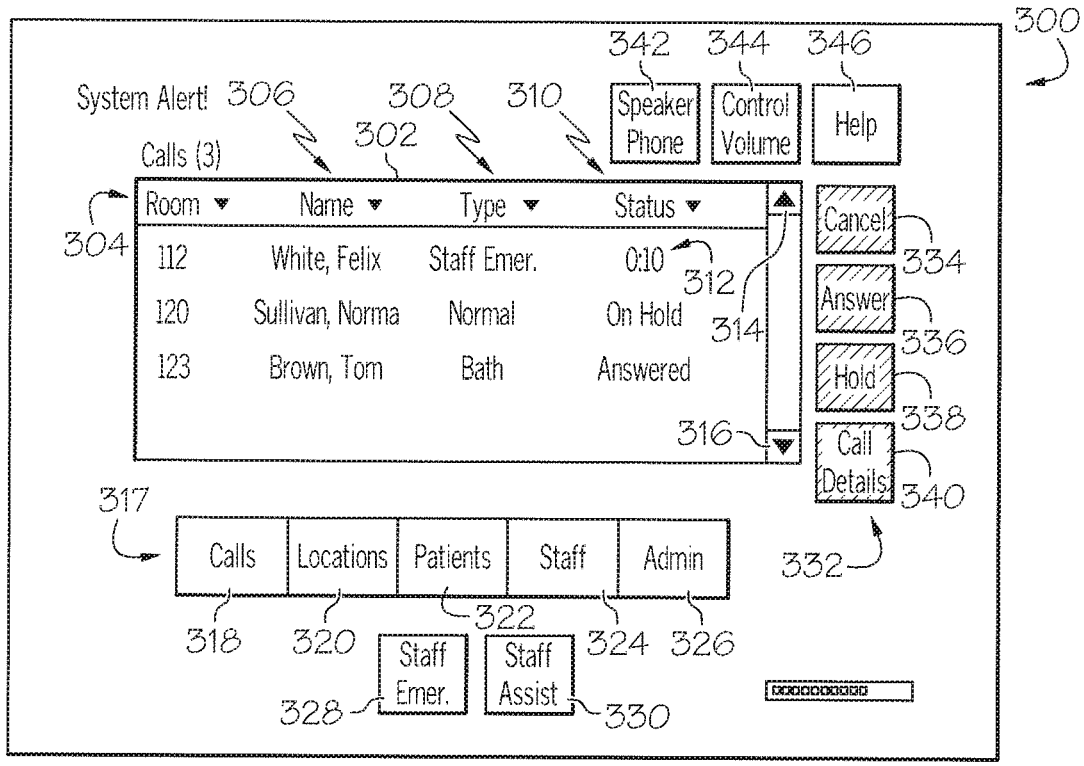
FIG. 4 is a screen shot of a Start screen that appears on a graphical audio station prior to a caregiver navigating to other screens, the Start screen having a list of incoming calls and having various menu icons that are pressed to navigate to other screens and to perform various functions.

FIG. 4 is a screen shot of an example of a Start screen 300 that appears on a graphical audio station prior to a caregiver navigating to other screens. Screen 300 becomes backlight when the locating circuitry senses the presence of a badge 60 of an approaching caregiver in some embodiments. Prior to sensing the caregiver, station 22 may still show screen 300 but without backlighting or station 22 may operate to show a blank screen or to show some other screen that doesn't show any or all of the information of screen 300. In other embodiments, the screen my become backlit when a user touches screen 300 or otherwise uses station 22.

Screen 300 includes a calls window 302 with a room column 304 listing the room numbers from which calls and/or alerts have been placed, a name column 306 showing the names of the patient in the associated room, a type column 308 indicating the type of alarm or call that has been placed, and a status column 310 indicating whether the call is being answered, is on hold, or has not yet been answered such as by having a timer 312 that counts up to indicate the seconds and minutes since the call has been placed but not yet answered or canceled. With regard to the status column 308, other statuses include "assigned waiting" which means the call was on a reminder list and came off of the reminder list at the time the reminder to make the call is to be displayed. Up and down arrows 314, 316 are provided in window 302 to permit a user to scroll up and down the list of calls in window 302 if there are more than five active calls, which in the illustrative embodiment, is the maximum amount of calls that appear in window 302 of screen 300 at once.

Start screen 300, as well as many other screens, include a menu 317 beneath window 302 with a Calls button 318, a Locations button 320, a Patients button 322, a Staff button 324, and an Admin button 326. Buttons 318, 320, 322, 324, 326 are touched to change the type of information being displayed in window 302 and/or on other areas of the display screen. Beneath menu 317 is a staff emergency button 328 which is touched to place a staff emergency call and a staff assist button 330 which is touched to place a staff assist call, which is a lower priority type of call than a staff emergency call. To the right of window 302 is a menu 332 which includes a cancel button 334 that is used to cancel a selected call, an answer button 336 that is used to answer a selected call, a hold button 338 that is touched to place a selected call on hold, and a call details button 340 that is touched to obtain more information about a selected call. To select a call, the caregiver touches the display screen in window 302 over any portions of the rows of information for a particular call and then presses the answer button 336 to answer the selected call. After the answer button 336 is pressed to answer a call, it becomes a "hang up" button which is touched to end the call. The cancel button 334 only becomes active if the caregiver uses another portion of the user interface of screen 300.

The order in which incoming calls are listed in window 302 is dictated by the priority level of the type of call received. Calls configured with the highest priority, such as a Code Blue call indicating that a patient is experiencing cardiac arrest, are displayed at the top of the list. If multiple calls having the same priority are received, the calls will be displayed from oldest to newest with the oldest of the calls at the top of the list or the top of the group of calls having the same priority in the event a higher priority call is also received. Other types of calls having no priority are displayed beneath those that have a priority level designated. The information in the rows of window 302 regarding the calls being received may be color coded. For example, in one embodiment, Code Blue calls are blue, emergency calls are red, and other calls are black.

As is apparent from the discussion of screen 300 of FIG. 4, a caregiver at a patient station 22 in a particular room, can answer a call in any other room listed in the calls window 302, which results in a two-way voice communication link being established between the patient station 22 in one room with the patient station 22 in another room. A caregiver at the master station 24 does not need to be involved in setting up or otherwise initiating or maintaining this room-to-room two-way voice connection. In the upper right hand corner region of screen 300 is a speaker phone button 342 which appears when screen 300 is associated with any stations 22, 24 mounted to a base unit 74 having a handset 76 to give the caregiver the option of operating the master or staff console 22, 24 as a speaker phone rather than needing to pick up the hand set 76.

Also in the upper right hand corner region of screen 300 is a Control Volume button 344 which, when touched, results in the display of a vertical slider for volume control of the call, and a Help button 346 which, when touched, results in the display of various help options selection buttons. Among the help options selection buttons include a first button that is touched to permit the caregiver to browse web pages hosted on servers of the healthcare facility on the display screen of station 22; a second button that is touched to permit the caregiver to browse web pages accessible via the Internet on the display screen of station 22; a third button that is touched to permit the caregiver to view on the display screen of station 22 multimedia content, such as videos, hosted on servers of the healthcare facility; and a fourth button that is touched to permit the caregiver to view on the display screen of station 22 multimedia content accessible via the Internet. The videos may include, for example, educational videos regarding equipment in the patient room and regarding medical procedures, but the videos are not limited to these and may be a video concerning any topic. The media content may include, for example, user manuals for equipment in the patient room or other medical information, but again, any type of media content is contemplated by this disclosure as potentially being accessible using station 22. The access to multimedia content just described is considered part of the "advanced services" functionality and not part of the "base nurse call system" functionality of station 22.

Figure 5:
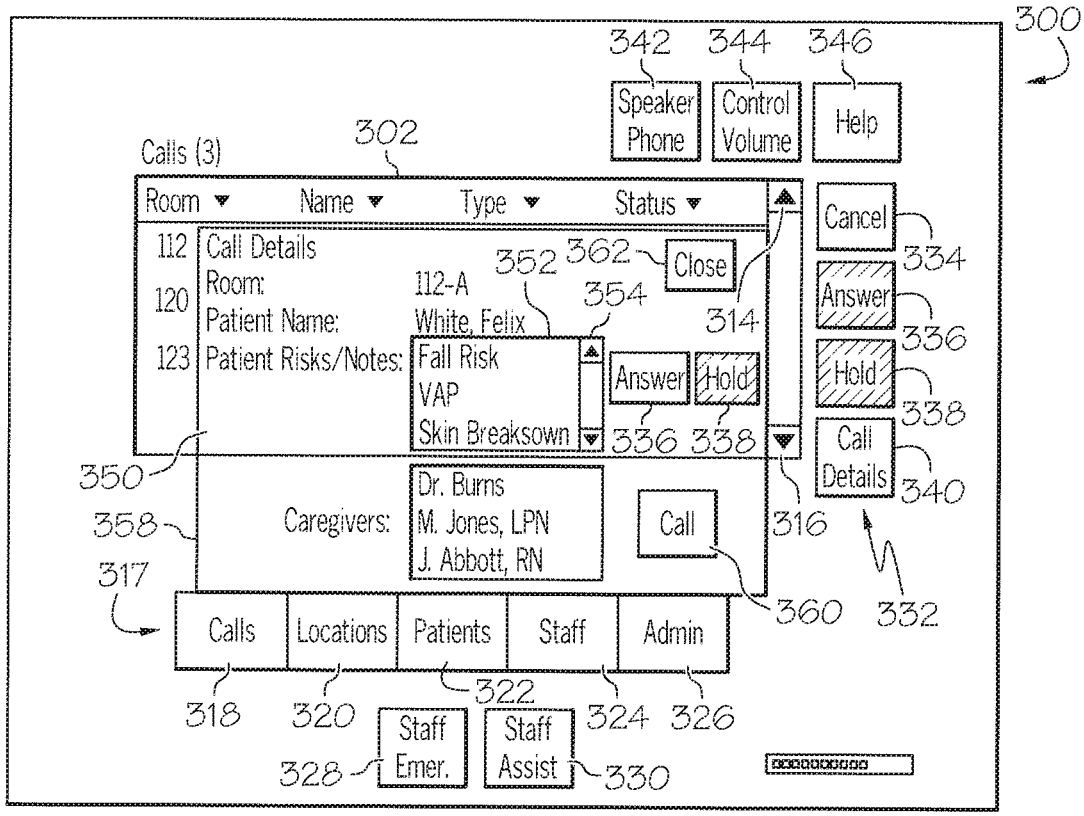
FIG. 5 is a screen shot of a Call Details screen that appears on a graphical audio station after a caregiver selects one of the calls and after a Call Details icon is selected by the caregiver.

In response to a caregiver touching the call details button, a call details window 350 appears on the display screen and partially overlaps window 302 as shown in FIG. 5. Call details window 350 includes text indicating the patient's name, the room number, and a notes text block 352 in which additional notes about the patient's condition or risks may be entered. In the illustrative example, block 352 includes the text "Fall Risk, VAP, Skin Breakdown" but of course caregivers may enter any notes of their choosing in block 352. VAP stands for "ventilator assisted pneumonia" in this example. Up and down arrows 354, 356 are provided for scrolling up and down if not all of the notes are viewable in block 352 at the same time.

Call Details window 350 also includes a Caregivers text block 358 which lists the various caregivers that have been assigned to the associated patient. In some embodiments, a caregiver using station 22 may be able to touch a Caregiver's name in block 358 and/or touch a Call button 360 which is adjacent block 358 and be presented with a menu of options for contacting that selected caregiver, including calling that caregiver's home phone number, office phone number, or cellular telephone number. Thus, this is an example of how station 22 may be used to place a call to a telephone, including a cellular telephone, located outside the healthcare facility. Window 350 also includes Answer and Hold buttons 336, 338 which are redundant to buttons 336, 337 of menu 332 and so similar reference numerals are used to denote these. However, only the buttons 336, 337 in window 350 are active when window 350 is displayed. If a user decides to contact one of the assigned caregivers using window 350, the user first touches the hold button 338 to place the current call on hold, after which button 338 becomes an "unhold" button. After the user places the call, the Call button becomes a "hang up" button which is touched to end the call. A Close button 362 is included in window 350 and may be touched to close out of window 350.

Figure 6:
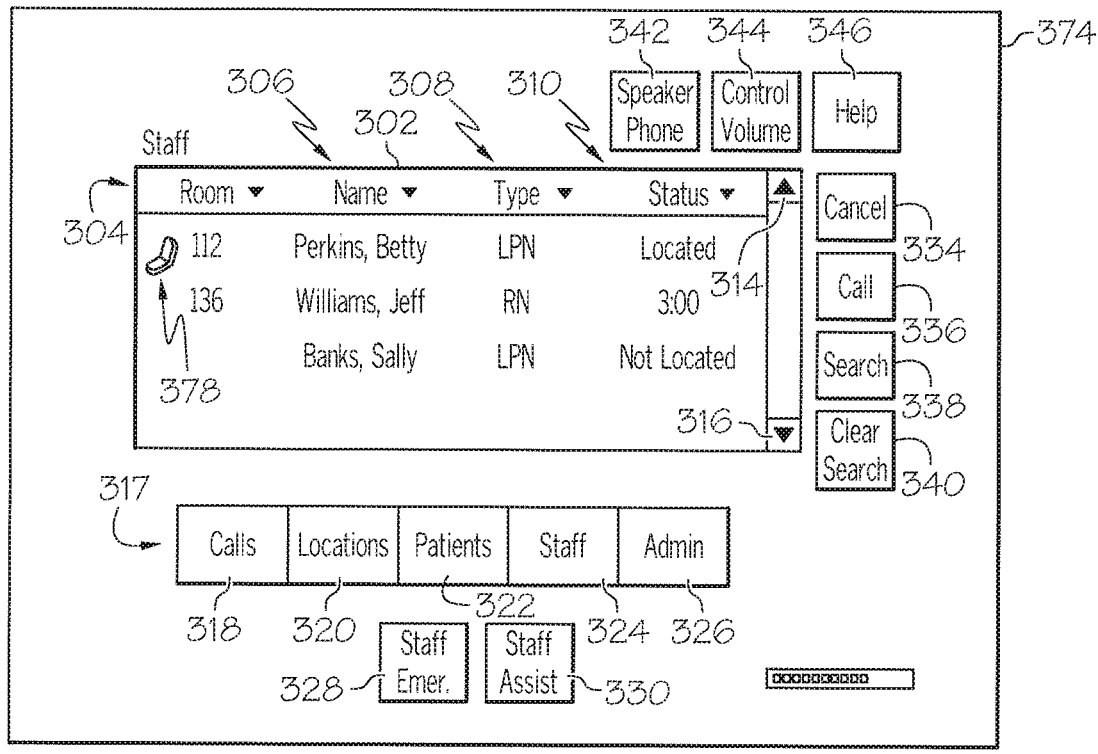
FIG. 6 is a screen shot of a Staff Screen that appears on the graphical audio station after a caregiver selects a Staff icon.
Figure 7:
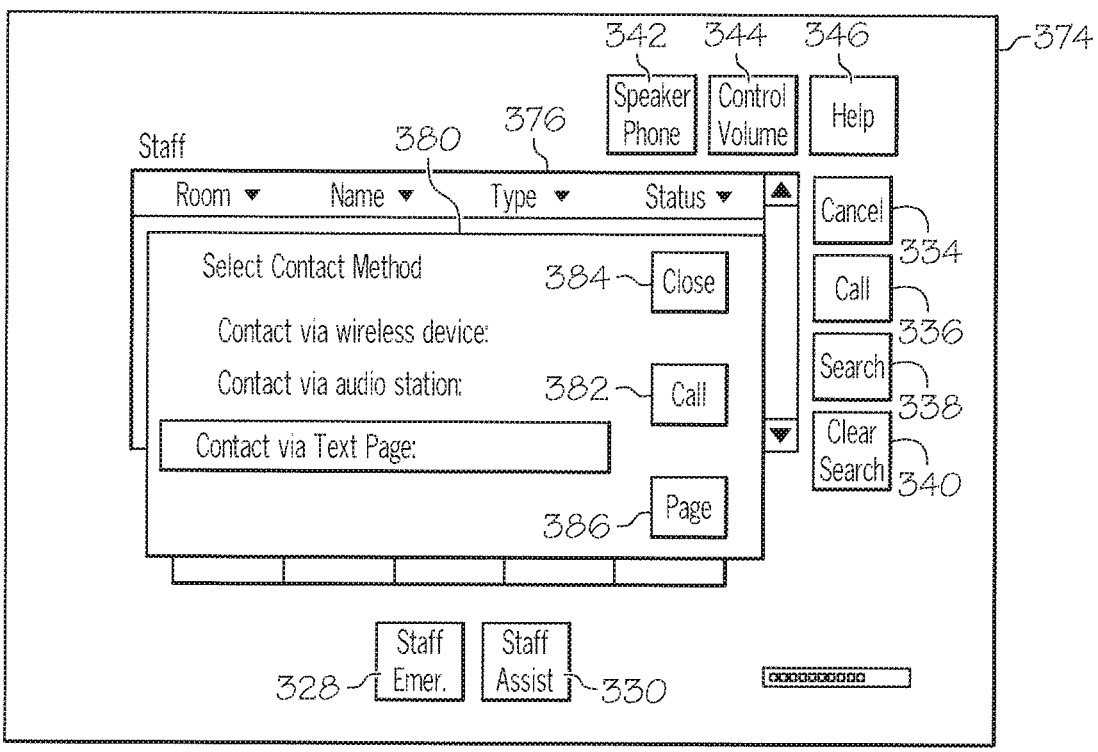
FIG. 7 is a screen shot of a Select Contact Method screen that appears on the graphical audio station in response to a staff person being selected on the Staff Screen, the Select Contact Method screen having a window listing the various options for contacting the selected staff person.

In response to a caregiver touching staff button 324, a Staff screen 374 appears on the display screen of graphical audio station 22 as shown, for example, in FIG. 6. Screen 374 has a staff window 376. Window 376 has room, name, type, and status columns 304, 306, 308, 310, as was the case with window 302 of screen 300. However, the information appearing in the rows of window 376 under columns 304, 306, 308, 310 correspond to staff members which are assigned to the particular nursing unit associated with the particular station 22 on which screen 374 appears. If desired, additional staff members, such a staff members in other nursing units or staff members associated with other portions of a healthcare facility that are not otherwise characterized as nursing units (e.g., emergency room, imaging, housekeeping, and maintenance, just to name a few) are listed. In some embodiments, if a staff person is located but is not in a patient room, the information in the room column 304 is left blank. This situation may occur, for example, if the staff person is in a hallway of the healthcare facility.

As indicated by a wireless phone icon 378 appearing next to the information in the first row of information in window 376 under columns 304, 306, 308, 310, the associated staff member (e.g., "Perkins, Betty" in the illustrative example as shown in the name column) is carrying a wireless communication device. In window 376, the status column 310 indicates whether or not a corresponding staff member has been located by an associated locating and tracking system of system 20. If a staff member is located, the location appears in the room column 304 for the associated caregiver. The type column 308 provides an indication of the type of caregiver. In the illustrative example, two of the listed staff members are LPN's and one of the listed caregivers is an RN. Other staff member types may include technician, housekeeper, doctor, therapist, and so on and suitable abbreviations of these types of caregivers may be used in type column 308. Up and down arrow icons 314 and 316 are provided to scroll to other staff member rows if more staff members are located than can be viewed in window 376 at the same time.

To contact a desired staff member appearing in window 376, a caregiver using station 22 touches any portion of the row associated with the desired staff member. In response to selection of a staff member to be contacted in this manner, a Select Contact Method 380 window appears on screen 374 and partially overlaps window 376 as shown, for example, in FIG. 7. A list of the various methods by which the selected staff member may be contacted appears in window 376. In the illustrative example, "Contact via wireless device"; "Contact via audio station"; and "Contact via Text Page" are the options that are listed in window 380. Depending on the available methods of contacting the caregiver, more or less similar such messages may appear in window 380.

The caregiver using station 22 (sometimes referred to as the "user") selects the desired call method option by touching that listed option on window 380. If the user selects the "Contact via wireless device option" or the "Contact via audio station option," the user then touches a call button 382 appearing in window 380 to initiate the call to the selected type of device (wireless device or audio station in the illustrative example). A Close button 384 also appears in window 380 and if a user touches button 384, window 380 closes and the start screen 300 reappears. If a staff member to be contacted is carrying a device that permits a text page or message, then the user first touches the "Contact via Text Page" option shown in window 380 and then touches a Page button 386. After button 386 is pressed, a keyboard (similar to keyboard 392 appearing in FIG. 8) is presented to the user on the display screen of station 22 for composing the text message to be sent to the staff member to be contacted. A text message window is provided on the display screen along with the keyboard so the user can view the text page message the user is creating. A Send message button is also presented to the user on the display screen of station 22 and the user presses the Send message button to send the text page after it has been composed.

Figure 8:
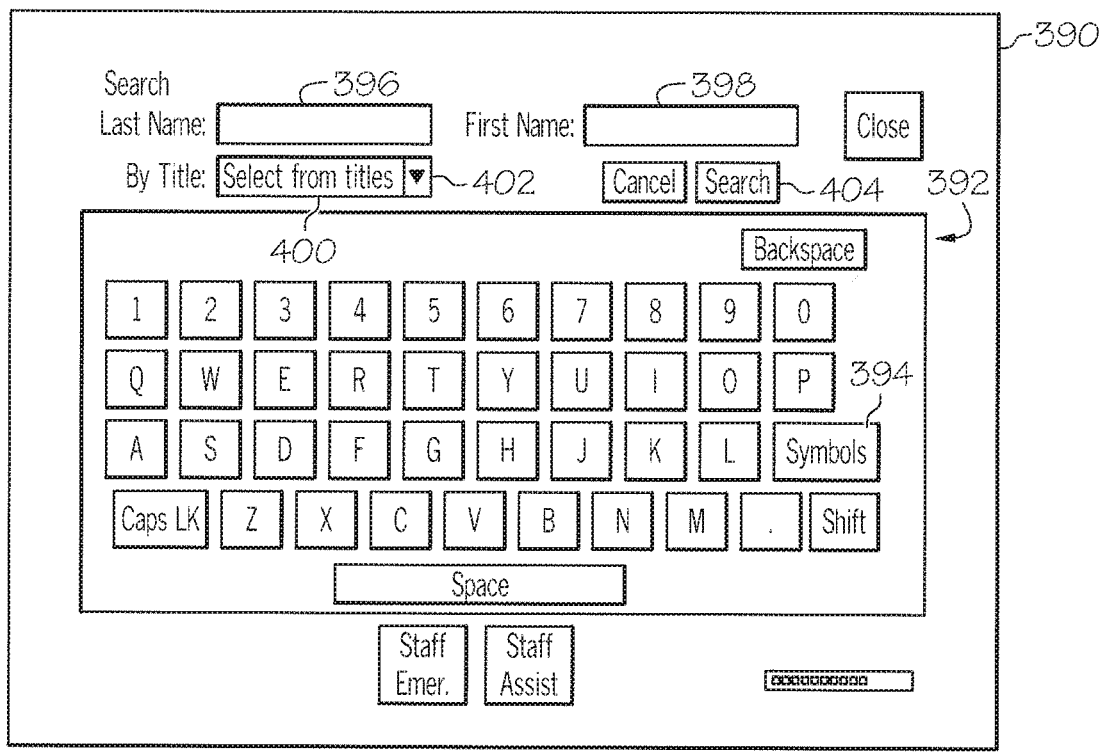
FIG. 8 is a screen shot of a Keyboard screen that appears on the graphical audio station when a Search icon is selected or when a caregiver selects the Contact via Text Page icon on the Select Contact Method screen.
Figure 9:
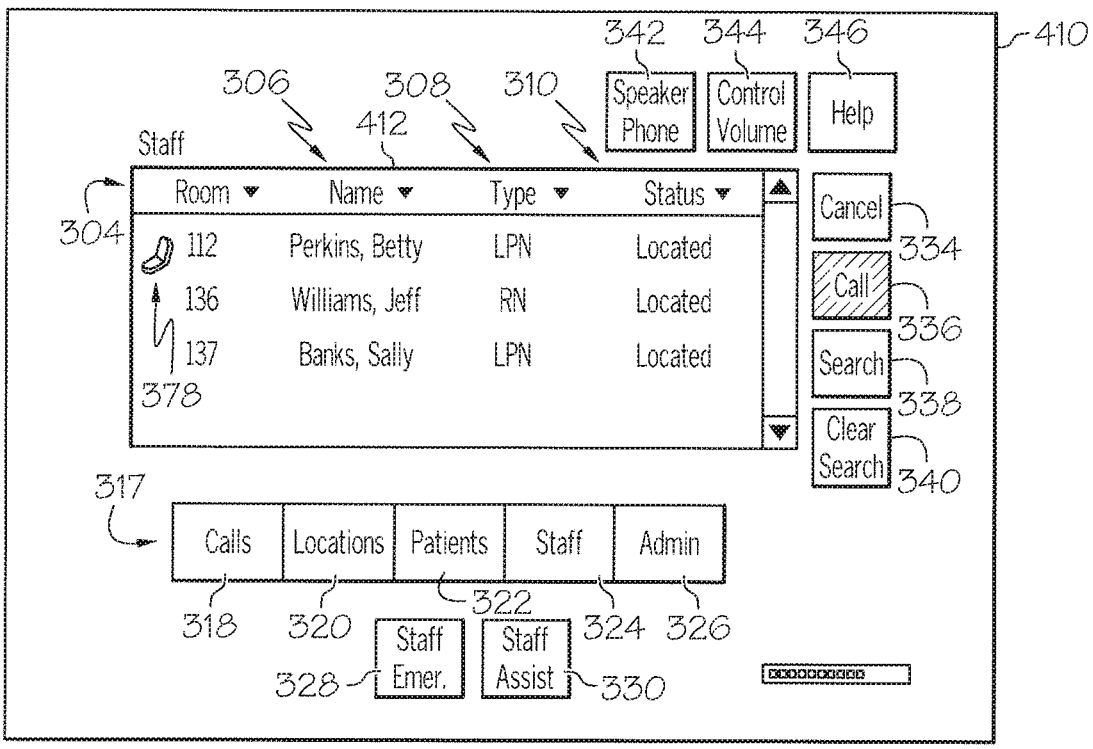
FIG. 9 is a screen shot of a Search Results page that appears on the graphical audio station after search criteria have been entered into one or more fields of the Keyboard screen.

In response to a search button 338 being touched, a Keyboard screen 390 appears on the display screen of graphical audio station 22 as shown, for example, in FIG. 8. Screen 390 has a keyboard 392 which, in turn, has a multitude of number and letter buttons which are laid out similar to a standard QWERTY keyboard. Keyboard 392 also has function keys such as a space bar button, a backspace button, a caps lock button, and a shift button. A symbols button 394 is included on keyboard 392 which is touched to change the function of the number buttons and letter buttons of keyboard 392 to symbol buttons which are touched to type corresponding symbols (e.g., !, @, #, $, %, &, *, etc.).

Window 390 has a last name text box 396 and a first name text box 398 into which the name of a particular staff member may be typed to search for the location in the facility of that individual staff member. A title box 400 has a drop down menu arrow 402 which, when pressed, results in a list of various staff titles (e.g., RN, LPN, doctor, physical therapist, housekeeper, transporter, maintenance, etc.) being present to the user on the display screen of station 22. The user then touches the screen on the type of staff persons the user wishes to search. To initiate the search after the search criteria are entered into one or more of boxes 396, 398, 400, the user presses a search button 404 of window 390. A cancel button 406 is provided on window and is pressed to cancel the search while it is running. Window 390 also has a close button 408 which is pressed to return to screen 374. After the search is complete, a Search Results screen 410 appears on the display screen of station 22 and includes a search results window 412 which lists the staff members that met the search criteria as shown, for example, in FIG. 9. The layout of window 412 is similar to window 376 of screen 374 discussed above and so like reference numerals are used to denote like features of these screens. The caregivers listed in window 412 may be contacted in the same manner as described above in connection with FIGS. 6 and 7.

Figure 10:
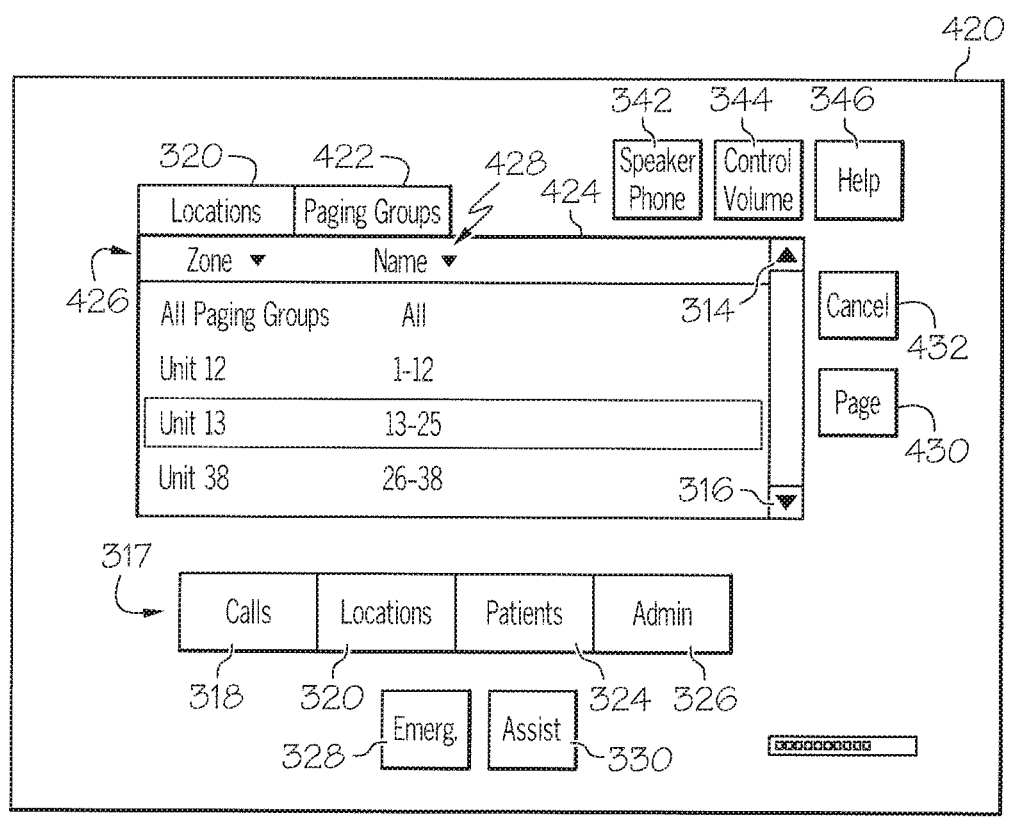
FIG. 10 is a screen shot of a Voice Page screen that appears on the graphical audio station after a Paging Groups tab is selected, the Voice Page screen having a list of various groups of graphical audio stations that are located in selected ones of the patient rooms and staff areas to which a voice page may be sent without sending the voice page to graphical audio stations that are not in the selected group.

Referring now to FIG. 10, a Voice Page screen 420 is shown. Screen 420 appears after locations button 320 is pressed and then after a paging groups tab 422 is pressed. In FIG. 10, the locations button 420 has moved from menu 317 and appears as a tab above alongside tab 422 above a paging groups window 424. Window 424 includes a zone column 426 and a name column 428. The rows under columns 426, 428 list the information about various subgroups of stations 22, 24, 122, 222 to which a voice page (i.e., similar to an overhead page or intercom page) can be sent from the station 22 at which the user is standing. Paging to a limited number of other stations 22 and/or stations 24, 122, 222 prevents unnecessary voice paging in areas for which there is no reason for such pages to be heard. This is an improvement over prior art nurse call systems in which paging from a patient room was not even possible, let alone to just a selected subset of other audio stations. Master stations 24 also have this type of "limited area" voice paging capability according to this disclosure, which is an improvement over prior art nurse call systems in which voice pages from a master station were sent to all audio stations associated with the master station.

To send a voice pale to a desired subgroup of other stations 22, 24, 122, 222, the user presses the row associated with the group of devices the user wishes to page and then presses a page button 430 of window 420. Pressing page 430 results in a one-way voice communication channel being created or opened to the devices associated with the selected group. A cancel button 432 is pressed to end the voice page. Additional screen shot examples appear in the Appendices of the written description of U.S. Provisional Patent Application No. 61/066,877 as mentioned previously.

As mentioned previously, a system 20 according to this disclosure is marketed by Hill-Rom Company, Inc. as the Hill-Rom® NaviCare® Nurse Call™ system. Additional details of the components and operability of that system are shown in the Appendices of the U.S. Provisional Patent Applications to which the present application claims the benefit. Each of those U.S. Provisional Patent Applications, including the Appendices of their written descriptions, will be available electronically (i.e., published) on the Patent Application Information Retrieval (PAIR) portion of the U.S. Patent and Trademark Office website when the present application is published.

Although certain illustrative embodiments have been described in detail above, variations and modifications exist within the scope and spirit of this disclosure as described and as defined in the following claims.

The invention claimed is:

1. A healthcare communication method implemented in a healthcare facility having a plurality of patient rooms, the healthcare communication method comprising:
providing a plurality of graphical audio stations, each of the patient rooms having at least one of the plurality of graphical audio stations located therein, each of the plurality of graphical audio stations having a graphical display screen,
displaying on the graphical display screen of at least one graphical audio station of the plurality of graphical audio stations a list of nurse calls for the room in which the at least one graphical audio station is located and for other rooms,
providing a master station communicatively coupled to each of the graphical audio stations, and
using user inputs of at least one graphical audio station of the plurality of graphical audio stations to conduct a search for a location within the healthcare facility of a specific caregiver.

2. The healthcare communication method of claim 1, wherein the user inputs comprise a keyboard shown on the graphical display screen of the at least on graphical audio station, and wherein using user inputs to conduct the search includes entering a name of the specific caregiver to be located using the keyboard.

3. The health care communication method of claim 2, wherein entering the name of the specific caregiver to be located includes entering the first name of the specific caregiver in a first box shown on the graphical display screen of the at least one graphical audio station and entering the last name of the specific caregiver in a second box shown on the graphical display screen of the at least one graphical audio station.

4. The healthcare communication method of claim 1, further comprising using the user inputs to conduct a search for locations of caregivers having specific job titles.

5. The healthcare communication method of claim 4, wherein the specific job titles include one or more of the following: registered nurse (RN), licensed practical nurse (LPN), doctor, physical therapist, housekeeper, transporter, and/or maintenance personnel.

6. The healthcare communication method of claim 1, further comprising using the user inputs of the at least one graphical audio station to establish a two-way communication link with the master station.

7. The healthcare communication method of claim 1, further comprising using the user inputs of the at least one graphical audio station to establish a two-way communication link with a wireless communication device carried by a caregiver.

8. The healthcare communication method of claim 1, further comprising using the user inputs of the at least one graphical audio station to establish a two-way communication link with a telephone of the healthcare facility or a telephone outside the healthcare facility.

9. The healthcare communication method of claim 1, wherein the graphical audio stations located in the patient rooms are each configured to receive a nurse call signal and further comprising communicating the nurse call signal to the master station.

10. The healthcare communication method of claim 1, further comprising providing a plurality of dome light assemblies, each dome light assembly being located in a hallway near a door of a respective patient room, and establishing a two-way communication link between the at least one graphical audio station and the master station using a circuit board located in a housing mounted near a respective one of the plurality of dome light assemblies.

11. The healthcare communication method of claim 1, further comprising receiving at the at least one graphical audio station an alert signal from at least one piece of equipment located in the respective patient room.

12. The healthcare communication method of claim 11, wherein the at least one piece of equipment comprises a hospital bed.

13. The healthcare communication method of claim 11, wherein the alert signal corresponds to an alarm condition of the at least one piece of equipment.

14. The healthcare communication method of claim 1, further comprising using the user inputs of the at least one graphical audio station to send a one-way voice page to a subset of the plurality of graphical audio stations.

15. The healthcare communication method of claim 14, further comprising using the user inputs of the at least one graphical audio station to select the subset of graphical audio stations to which the one-way voice page is to be sent.

16. The healthcare communication method of claim 14, further comprising using the user inputs of the at least one graphical audio station to send the one-way voice page to the master station.

17. The healthcare communication method of claim 1, further comprising using the user inputs of the at least one graphical audio station to send a text message to a wireless device carried by a caregiver.

18. The healthcare communication method of claim 1, further comprising using the user inputs of the at least one graphical audio station to select a contact method from among different contact methods for contacting the specific caregiver.

19. The healthcare communication method of claim 18, further comprising providing locating equipment operable to determine whereabouts of caregivers in the healthcare facility and wherein the different contact methods includes contacting a specific one of the plurality of graphical audio stations corresponding to the location within the healthcare facility of the specific caregiver.

20. The healthcare communication method of claim 1, further comprising using the user inputs of the at least one graphical audio station to perform at least one or more of the following functions: acknowledge alerts or nurse calls, answer alerts or nurse calls, and/or cancel alerts or nurse calls.

* * * * *